US006197593B1

(12) United States Patent
Deka et al.

(10) Patent No.: US 6,197,593 B1
(45) Date of Patent: Mar. 6, 2001

(54) METHOD FOR ENUMERATING BLOOD CELLS

(75) Inventors: Chiranjit Deka, Miami; James L. Wyatt, Plantation; Kristie M. Gordon, Coral Gables, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/175,494

(22) Filed: Oct. 20, 1998

(51) Int. Cl.$^7$ ........................................ G01N 33/48
(52) U.S. Cl. .......................... 436/63; 436/164; 436/172; 436/800; 422/73; 356/39
(58) Field of Search ........................ 436/63, 164, 172, 436/800; 422/73; 250/461.2; 356/39

(56) References Cited

U.S. PATENT DOCUMENTS

| | | |
|---|---|---|
| 4,400,370 | 8/1983 | Kass . |
| 4,882,284 | 11/1989 | Kirchanski et al. . |
| 5,206,143 * | 4/1993 | Horan ................................ 435/7.24 |
| 5,296,378 * | 3/1994 | Sakata ................................... 436/63 |
| 5,360,739 | 11/1994 | Fan et al. . |
| 5,639,666 | 6/1997 | Shenkin . |

OTHER PUBLICATIONS

J.T. Verdeyen, "Detection of Optical Radiation", *Laser Electronics*, 2$^{nd}$ Edition, Prentice Hall, Chp. 16, pp. 565–599 (1989).
Millard, P.J., et al., "Fluorescence–Based Methods for Microbial Characterization and Viability Assessment", *Biotechnol. Int'l.*, 1:291–296 (1997).
H. Shapiro, Practical Flow Cytometry, 3$^{rd}$ edit., Wiley–Liss, New York (1995).
Davis, et al., "Clinical Flow Cytometric Reticulocyte Analysis", *Pathobiology*, 58:99–106 (1990).
T.G. Hoy, "Flow Cytometry : clinical applications in haematology", *Bailliere's Clin. Haemat.*, 3:977–988 (1990).
Barlogie, et al., "Cellular DNA Content as a Marker of Neoplasia in Man", *Amer. J. Med.*, 69:195 (1980).
Belosevic, et al., "Nucleic Acid Stains as Indicator of Cryptosporidium parvum Oocyst Viability", *Int'l. J. Parasitol.*, 27:787 (1997).
H.J. Tanke, "Reticulocytes and Mature Erythrocytes", *Flow Cytometry in Hematology*, Chp. 2.1, pp. 75–93 (1992).

* cited by examiner

*Primary Examiner*—Maureen M. Wallenhorst
(74) *Attorney, Agent, or Firm*—Mary E. Bak; Mitchell E. Alter

(57) ABSTRACT

A method for enumerating and distinguishing between blood cell populations in a biological sample includes the steps of contacting a biological sample with a cell membrane-permeant, red-excited, nucleic acid binding dye, without significantly disrupting the integrity of the cells; exciting this sample with light in one red wavelength; and measuring fluorescence emitted from different cell populations in the sample. This method is particularly desirable for enumerating different WBC subpopulations using flow cytometry. This method is also useful for enumerating reticulocytes or NRBC or mature RBC. This method is enhanced by pretreating the sample with a nucleic acid-specific blocking agent. Dyes useful in this method include, without limitation, SYTO®17 dye, SYTO®159 dye, SYTO®60 dye, SYTO®61 dye, SYTO®62 dye, SYTO®63 dye, and SYTO®64 dye.

18 Claims, 9 Drawing Sheets

METHOD FOR ENUMERATING BLOOD CELLS

FIELD OF THE INVENTION

This invention generally relates to methods of hematological analysis, and relates, more specifically to methods for leukocyte subpopulation and other blood cell population differentiation employing a cell permeant red-excited nucleic acid stain.

BACKGROUND OF THE INVENTION

White blood cell (WBC), or leukocyte, analysis is the enumeration, identification and differentiation of the various subpopulations of leukocytes, such as neutrophils, eosinophils, basophils, and monocytes, lymphocytes, myelocytes, metamyelocytes, blast cells, band cells, etc., in normal and pathologic human blood, plasma or serum. Such analysis is a valuable component of diagnostic hematology, useful in the diagnosis of disease, such as leukemia, the monitoring of treatment, such as chemotherapy, the determination of the need for surgery, and other conditions such as hemorrhage, anemia, monitoring bone marrow transplantation, and other disorders involving blood cell production [See, for example, U.S. Pat. No. 5,360,739; H. Shapiro, Practical Flow Cytometry, $3^{rd}$ edit., Wiley-Liss, New York (1995); Davis et al (1990) Pathobiol., 58:99–106; and Hoy, (1990) Bailliere's Clin. Haemat., 3:977–988, among others].

Presently, automated leukocyte analysis is conducted in hematology analyzers by utilizing differences in cell morphology or antibody reactivity. The detection of morphological differences between cell populations uses physical measurements including light scatter, direct current (DC) impedance or radio frequency (RF) conductivity of individual cells or even differential absorption or fluorescence of cells stained with certain specific dyes. Leukocyte analysis methods have used reagents or dyes that specifically stain certain leukocytes a different color, and thus enable one to distinguish between different leukocyte populations. Such multiple color dye stains include Romanowski and Wright stains.

Analysis based on antibody reactivity employs specificity of different antibodies to different antigens that may be expressed in different cell types. A measure of such reactivity is obtained through either fluorescence signal from dyes conjugated to the antibody or signature light scatter signal from particles conjugated to the antibody. While a sensitive method, it can be quite costly and complex, requiring careful and long incubation of reagent in the blood sample.

Alternatively, leukocytes may be analyzed based on their different nucleic acid content. DNA content measurements were used clinically for diagnosis and for determination of effects of drugs on tumor cell proliferation kinetics [M. Andreef, Impulscytophotometrie. Berlin, Springer, 1975]. DNA content abnormalities are common in cancer and leukemia [B. Barlogie et. al. Amer. J. Med. 69:195, 1980]. Leukocyte analysis based on nucleic acid content of cells using metachromatic dye stains, i.e., dyes that absorb and/or fluoresce differentially when bound to DNA and RNA nucleic acids, has been suggested. See, e.g., U.S. Pat. No. 4,440,370. As a result, based on DNA or RNA content, different blood cell populations absorb, or fail to absorb, a single metachromatic dye in some unique manner so that each dye-sorbed cell reflects an individual and different light spectra. Such dyes include, without limitation, basic orange 21 (CI#48035), basic red 13, basic red 36, basic red 49, basic violet 7, basic violet 16, among others, and several classes of oxazine dyes described in U.S. Pat. No. 4,400,370, cited above. The process of leukocyte differentiation with metachromatic dyes is quite costly, due to the requirement for at least two photomultiplier tubes (PMTs).

U.S. Pat. No. 4,882,284 describes a method for discriminating WBCs from RBCs and platelets in a whole blood sample by utilizing a metachromatic red light absorbing fluorescent dye, i.e., an oxazine, a red light source and detectors. The dyes described therein include oxazine 170 (also known as oxazine 720). According to this method, the red cells are not lysed. Thus, this method suffers from some disadvantages. Inability to lyse the red cells requires too large of a data collection if the goal is the analysis of leukocytes, due to the 1000:1 ratio of RBC to WBC in normal blood. This aspect of the '284 process makes it undesirable for automated analysis. In another method, U.S. Pat. No. 5,360,739 also describes the use of a unique oxazine dye, oxazine 750, to identify and enumerate reticulocytes. A significant disadvantage of the methods of the '284 and '739 patents is that dyes such as oxazine 720 and oxazine 750, are brightly fluorescent, whether or not they are bound to nucleic acid. In fact, due to their bright fluorescence in free solution, both oxazine 720 and oxazine 750 have been used as gain media in dye lasers. For flow cytometric analysis of cells, however, bright fluorescence of unbound molecules is a highly undesirable attribute for dyes used to stain specific components within the cell. Such fluorescence creates a background noise from non-specifically bound or unbound molecules and diminishes the specificity of detection for the targeted components in the cells.

Certain known dyes such as TOTO-1® dye, TOTO-3® dye, TOPRO-3® dye, etc., and the new SYTO® dyes, are also capable of staining both DNA and RNA nucleic acid in a cell. SYTO® dyes are red fluorescent nucleic acid stains in a solvent of dimethylsulfoxide (DMSO), which are commercially available (Molecular Probes, Inc., Eugene, Oreg.). These nucleic acid dyes are sold under the trademarks SYTO®17, and 59 through 64. These stains have been reportedly employed for detection of live or dead bacteria, e.g., C. parvum viability [M. Belosevic et al, (1997) Int'l. J. Parasitol., 27:787] and in methods for microbiological characterization and viability assessment [P. J. Millard et al, (1997) Biotechnol. Int'l., 1:291]. The manufacturer describes these stains as cell-permeant nucleic acid stains that differ from each other in characteristics including cell permeability, fluorescence enhancement upon binding, and in excitation and emission spectra. Eukaryotic cells incubated with SYTO® dyes reportedly show cytoplasmic or mitochondrial staining as well as nuclear staining (Molecular Probes product insert). These dyes have also been reported to produce minimal background fluorescence from unbound dye and enhancement of fluorescence quantum yield of DNA and RNA bound dye molecules compared to unbound dye molecules. However, none of these dyes have been suggested as possible agents for WBC or reticulocyte/mature RBC differential analysis.

In view of the importance of blood cell population analyses, e.g., leukocyte differentiation, there exists a continuing need in the art for methods which improve blood cell differentiating technology, such as by enabling rapid staining and differentiation of intracellular nucleic acids and permitting ready and accurate detection of white blood cell (WBC) subpopulations and other blood cell populations, such as RBC and reticulocytes.

SUMMARY OF THE INVENTION

The present invention meets the need in the art by providing methods for improving blood cell differentiating technology by employing dyes, not previously taught as useful for this purpose, which have the advantages of rapid staining for use in automated hematology systems, the ability to operate in the presence of reagents for eliminating RBCs from WBC analysis samples, and minimal background fluorescence from unbound dye. The invention provides an efficient and clinically useful rapid method for leukocyte analysis based on nucleic acid detection using a red-excited dye, which makes low cost DNA and RNA acid based leukocyte analysis feasible using low cost illumination sources, such as diode laser or red HeNe laser.

Thus, in one aspect, the present invention provides an improved method for differentiating between leukocyte populations by fluorescence flow cytometry. More specifically, in one embodiment, the method permits enumerating and distinguishing between different white blood cell (WBC) subpopulations in a biological sample based on nucleic acid staining and fluorescence measurement at one wavelength and with high specificity for nucleic acid. This method is accomplished by contacting a biological sample containing two or more WBC populations and optionally other cell populations, e.g., red blood cells ( RBC), reticulocytes, etc., with at least one cell membrane-permeant, red-excited dye, without significantly disrupting the integrity of said cells. The sample is illuminated or excited with light in the red wavelength; and the resulting fluorescence emitted from different leukocyte populations in the sample is measured. The fluorescence emitted from the different WBC populations is distinguishable. The dye used in this method may be selected from a group of red-excited dyes, such as SYTO®17 dye, SYTO®59 dye, SYTO®60 dye, SYTO®61 dye, SYTO®62 dye, SYTO®63 dye, and SYTO®64 dye (Molecular Probes, Inc.). Also according to this method, the excitation light source may be a diode laser, a light emitting diode (LED), an ion laser or a lamp.

In another embodiment, this method permits the differentiation of reticulocytes from mature red cells by fluorescence flow cytometry based on nucleic acid staining and fluorescence measurement at one wavelength and with high specificity for nucleic acid. This method is accomplished by contacting a biological sample containing reticulocytes and mature RBC and optionally other cell populations, with at least one cell membrane-permeant, red-excited dye for about one minute, without significantly disrupting the integrity of said cells. The sample is illuminated or excited with light in the red wavelength; and the resulting fluorescence emitted from the reticulocytes and mature RBC populations in the sample is measured. Reticulocytes are distinguishable from the mature RBC populations in the sample due to the fluorescence from the RNA-bound dye in the reticulocytes. The dye used in this method may be selected from the above-listed red-excited dyes. Also according to this method, the excitation light source may be a diode laser, an LED, an ion laser or a lamp.

In still another aspect, this invention provides a method for selectively enhancing the capacity of a selected dye to specifically detect a nucleic acid component in a sample by pre-staining the cells with secondary reagents that preferentially bind to, or digest, other nucleic acid components within the cell. In one embodiment, the method involves enumerating and distinguishing between different WBC subpopulations in a biological sample based on nucleic acid staining and fluorescence measurement at one wavelength. This method is accomplished by contacting a biological sample containing two or more cell populations and optionally other cell populations, as described above, with a RNA or DNA specific blocking reagent and then contacting the sample with at least one cell membrane permeant, red-excited dye for about one minute, without significantly disrupting the integrity of said cells. The sample is illuminated or excited with light in the red wavelength; and the resulting fluorescence emitted from different leukocyte populations in the sample is measured. The results obtained by measuring the fluorescence of the red-excited dye at one wavelength following pre-exposure to the blocking agent, are enhanced. Suitable blocking agents include RNA blocking agents, DNA blocking agents, GC-base pair specific DNA dyes, AT-base pair specific DNA dyes, and enzymes that selectively digest DNA or RNA.

In still another aspect, the invention provides a method for differentiating reticulocytes, which contain RNA, or nucleated red blood cells (NRBC), that contain DNA, from mature red blood cells that contain neither DNA nor RNA, by fluorescence flow cytometry comprising contacting a biological sample containing reticulocytes NRBC and mature RBC and optionally other cell populations, as described above, with a RNA or DNA specific blocking reagent. A DNA blocking reagent is preferred to block the DNA in NRBC to enhance accuracy of reticulocyte enumeration. A RNA blocking agent is preferred to block the RNA in reticulocytes to enhance accuracy of NRBC enumeration. Then the sample is contacted with at least one cell membrane-permeant, red-excited dye for about one minute, without significantly disrupting the integrity of said cells. The sample is illuminated or excited with light in the red wavelength; and the resulting fluorescence emitted from the reticulocyte or NRBC, and mature RBC populations in the sample is measured. The results obtained by measuring the fluorescence of the red-excited dye at one wavelength following pre-exposure to the blocking agent, are enhanced. Suitable blocking agents include RNA blocking agents, DNA blocking agents, GC-base pair specific DNA dyes, AT-base pair specific DNA dyes, and enzymes that selectively digest DNA or RNA.

Other aspects and advantages of the present invention are described further in the following detailed description of the preferred embodiments thereof, reference being made to the accompanying figures.

BRIEF DESCRIPTION OF THE DRAWINGS

FIG. 6A is a dot plot showing light scatter versus fluorescence signals for red cells stained with SYTO®62 stain according to the present method. The rectangular gate is designed to distinguish between non-fluorescent mature red cells and fluorescent reticulocytes. Reticulocytes are resolved from the mature red cells by the high fluorescence signal from the RNA bound SYTO®62 stain. This figure shows results for a sample having low reticulocyte counts.

FIG. 6B is a one dimensional histogram of the sample described in FIG. 6A; the signal from the reticulocytes appear as a distinct tail on the right hand side.

FIG. 6C is a dot plot showing light scatter versus fluorescence signals for red cells stained with SYTO®62 stain according to the present method, as described for FIG. 6A, but for a sample having a relatively high reticulocyte count. Notice the appearance of cells in the gate that distinguishes fluorescent reticulocytes in this sample.

FIG. 6D is a one dimensional histogram of the sample described in FIG. 6C; the signal from the reticulocytes appear as a distinct tail on the right hand side.

FIG. 6E is a dot plot showing light scatter versus fluorescence signals for red cells stained with SYTO762 stain according to the present method, as described for FIG. 6A, but for a sample having a relatively high reticulocyte count. Notice the appearance of cells in the gate that distinguishes fluorescent reticulocytes in this sample and in FIG. 6A.

DETAILED DESCRIPTION OF THE INVENTION

Figure 1A:
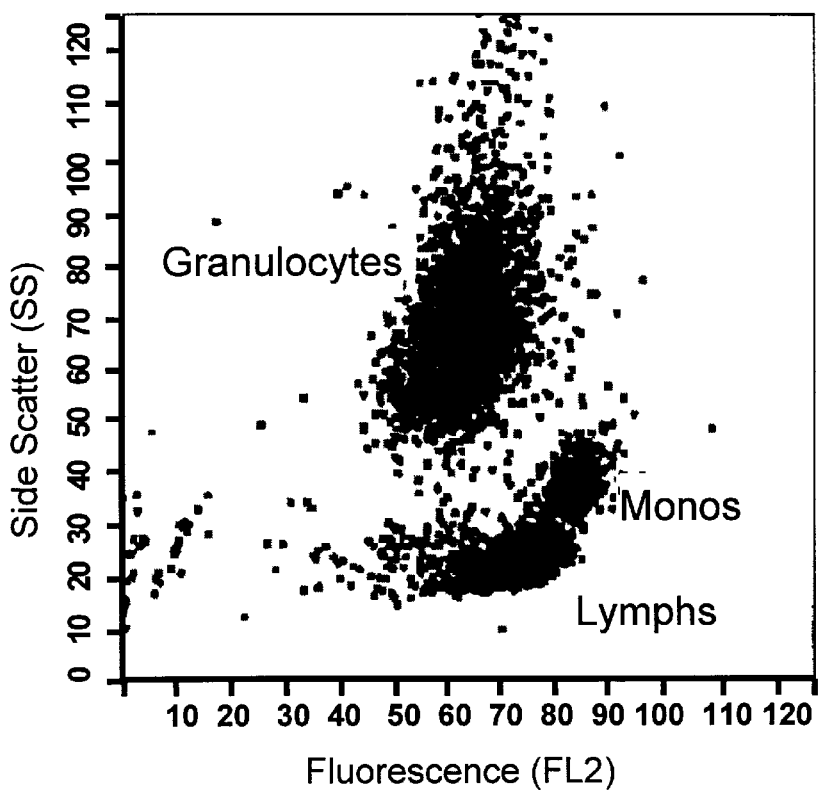
FIG. 1A is a two dimensional dot plot showing side light scatter vs. fluorescence signals for a sample of WBC stained with SYTO®59 stain and measured at one wavelength according to the present invention. Granulocytes, monocytes and lymphocytes are shown differentially stained.

The present invention meets the need in the art by providing a method for enumerating and distinguishing blood cell populations in a biological sample by surprisingly using a single, membrane-permeant, red-excited dye. In another embodiment of this method, the fluorescent distinctions observed by use of the dye are enhanced by employing nucleic acid blocking agents.

As a method for leukocyte analysis, the method employs the step of contacting a biological sample containing two or more white blood cell (WBC) populations with a cell membrane-permeant, red-excited, non-metachromatic dye, which is able to stain the cell contents without significantly disrupting the integrity of the cells. The binding of the dye to the cells distinguishes between various subpopulations of white blood cells. The subpopulations of WBC include, for example, lymphocytes, neutrophils, eosinophils, basophils, monocytes, immature granulocytes, abnormal lymphocytes, blast cells, band cells, myelocytes, promyelocytes and metamyelocytes.

Other cells may be present in the sample. Advantageously, no cell fixation procedures are necessary. The sample may be a whole blood sample, or a blood component, such as plasma or serum.

As a method for distinguishing reticulocytes (which contain RNA) or nucleated red blood cells ((NRBC) which contain DNA), from mature red blood cells (which contain neither DNA nor RNA), the method employs the step of contacting a biological sample containing reticulocytes, NRBC and mature RBC populations with a cell membrane-permeant, red-excited, non-metachromatic dye, which is able to stain the cell contents without significantly disrupting the integrity of the cells. The binding of the dye to the cells distinguishes between various populations of blood cells. Other cells may be present in the sample. Advantageously, no cell fixation procedures are necessary. The sample may be a whole blood sample, or a blood component, such as plasma or serum.

The selected dye is preferably one of the SYTO® dyes [Molecular Probes, Inc., Eugene, Oreg.], which are red fluorescent nucleic acid stains in a solvent of dimethylsulfoxide (DMSO). These nucleic acid dyes are sold under the trademarks SYTO®17, and 59 through 64. When used in the methods described herein, these dyes can distinguish blood cell populations based on differences of relative intensities of fluorescence from different cell types at the same wavelength range. This difference can be due to different relative amount of DNA and RNA in different types of cells, different relative binding affinity of a specific SYTO® dye to DNA and RNA within a given cell type and different fluorescence quantum yield (QY; number of fluorescence photons emitted by a molecule per absorbed photon) enhancement of the RNA and DNA bound species of the same SYTO® dye. Further advantages of the use of these dyes in the methods described herein are the rapidity of cell staining, which provides these methods with the capacity for automation, and the ability to work in the presence of RBC lysing agents or the nucleic acid blocking agents described below.

When employed in the methods of white cell or reticulocyte enumeration according to this invention, the concentration of the SYTO dye used is between about 5 $\mu$M to about 5 mM. Samples are prepared (see Examples 1 and 2 below) by adding 10 $\mu$L SYTO dye (original stock concentration of 5 mM) into 100 $\mu$L of whole blood, and incubating the samples for about one minute. This corresponds to a final concentration of 500 $\mu$M SYTO dye in the sample. Incubation times may range from about 30 seconds to about 5 minutes, but 1 minute has been found to be adequate for this step of the method. As demonstrated in Example 1 below, 10 $\mu$L dye per 100 $\mu$L blood with 1 minute staining was sufficient to observe differential staining between three WBC subpopulations. Further the incubation temperature ranges between 18° C. to 40° C., but may ordinarily be room temperature, i.e., about 23° C. Another desirable aspect of this invention is that optionally, in WBC analysis, any red cells in the biological sample may be lysed by standard techniques. Lysis of the red cells does not adversely affect this method. The same rapid staining method may be employed in distinguishing NRBC and reticulocytes, although the optimum concentration of the dye for this application will vary.

After the cell populations in the sample are adequately stained, the sample is exposed to (i.e., excited with) light in a single red wavelength. The wavelength range for excitation is desirably between 550 nm and 650 nm. For example, in Examples 1 and 2 below, the wavelength employed for excitation was 632.8 nm. An excitation source of light in the red wavelength may be a red diode laser, a high power light emitting diode (LED), an ion laser, an upconversion fiber laser, an upconversion solid state laser, a dye laser, and a lamp. Excitation sources such as diode lasers or HeNe lasers which emit light in the red wavelength are generally cheaper than conventional argon lasers employed in fluorescence measurements of dyes which absorb in the blue or green wavelengths. This is one of the advantages of the methods of this invention. However, it should be noted that selection of the particular red wavelength or excitation source is not to be considered a limitation of this invention.

The fluorescence emitted from different WBC populations stained with dye excited by the single red wavelength or from reticulocytes and mature RBC, as the case may be, is measured. Preferably this measurement occurs in an automated flow cytometer. Automated flow cytometers are well known in the art, e.g., the COULTER® XL™ flow cytometer [Coulter Corporation, Miami, Fla.]; the present invention is not limited to the use of any particular flow cytometer. The measuring apparatus may measure fluorescence on a cell-by-cell basis, may measure fluorescence simultaneously with other parameters, such as light scatter, DC and RF. The measuring apparatus may also include one or more PMTs, a semiconductor based PIN detector [see e.g., Joseph T. Verdeyen, in *Laser Electronics*, $2^{nd}$ Edition, Prentice Hall, 1989], or a semiconductor based Avalanche Photo Diode (APD) detector. Alternatively, such measurement may be made manually or in an automated fashion using a fluorescent microscope.

According to the methods of this invention, fluorescence emitted from one white cell population is distinguishable from the fluorescence emitted from other white cell populations in the same sample. See, e.g., Example 1 and FIGS. 1A, 1B, 2A and 2B. Also according to the methods of this invention, fluorescence emitted from reticulocytes is distinguishable from the fluorescence emitted from mature RBC or NRBC. See, e.g., Example 3.

The discovery by the present inventors that such red permeant, DNA dyes show differences in fluorescence among a number of WBC subpopulations was surprising, as it is a finding quite contradictory to the well known principle that a DNA specific dye should not be able to differentiate normal WBC subpopulations because each mature and normal WBC is supposed to have same amount of DNA. Without wishing to be bound by theory, the inventors theorize that because these dyes, e.g., the SYTO® dyes, stain not only the DNA in the nucleus, but also the RNA and cytoplasm of the cell, and because the latter component is different for each population, the total number of dyes molecules bound to each population is not the same, even if the DNA content is the same. As a result, the total fluorescence intensity varies from population to population. Additionally, it is possible, that the rapid kinetics of the present experiments of Examples 1 and 2, conducted as they were in a timed staining protocol, also plays a role in differential uptake of the dye in different blood cell populations.

Thus, the method of this invention displays a number of notable advantages in comparison to the prior art. These red-excited dyes permit the use of a cheaper excitation source than argon lasers. Further, these dyes are very weakly fluorescent in the unbound state. As a result, problems associated with background fluorescence is minimal, and WBCs and reticulocytes can be detected with high specificity. A single wavelength can be employed in this determination, thus improving the speed with which the hematological evaluation can be accomplished. Additionally, because this method does not significantly perturb the integrity of the cell membrane unlike methods that use cell impermeant dyes, the same samples can be employed for other measurements, such as antibody based analysis for leukocyte analysis and cell-by-cell hemoglobin on detected reticulocytes, etc., thereby limiting the amount of biological material necessary to conduct necessary diagnostic tests.

In still another embodiment, the present invention provides a novel method for enumerating and distinguishing blood cell subpopulations in a biological sample using the same red permeant dyes described above. This method employs a cell population shifting step which uses a nucleic acid-specific blocking agent to enhance the efficiency of the measurement of the desired cell subpopulation. This method may so be employed to measure WBC or RBC, NRBC or reticulocyte populations, depending on the identity of the blocking agent. Thus, the method includes the step of contacting a biological sample, such as the samples described above, which contain two or more white or red blood cell populations, with a selective nucleic acid-specific blocking agent.

The nucleic acid-specific blocking agent may be a DNA blocking agent, which when used in this method, will enhance the measurement of RNA containing cell populations, such as immature white blood cells or reticulocytes. For example, a DNA blocking reagent is preferred to block the DNA in NRBC to enhance accuracy of reticulocyte enumeration. Such DNA blocking agents include DNA dyes which fluoresce in wavelengths other than the red wavelength, such as the exemplary DNA specific-dye Ho-33342 [Sigma B2261] which is known to the have specific affinity for AT base pairs of DNA or the 7-ADD dye [Molecular Probes, Inc.], known to have specific affinity for GC base pairs of DNA. Alternatively, the DNA blocking agent can be an enzyme that selectively digests DNA, such as Dnase [Sigma]. One of skill in the art may readily select other DNA blocking agents.

The nucleic acid-specific blocking agent may be a RNA blocking agent, which when used in this method, will enhance the measurement of DNA containing cell populations, such as red blood cells and mature WBC. As another example, an RNA blocking agent is preferred to block the RNA in reticulocytes to enhance accuracy of NRBC enumeration. Such RNA blocking agents include RNA dyes which fluoresce in wavelengths other than the red wavelength. Alternatively, the RNA blocking agent can be an enzyme that selectively digests RNA, such as RNase. One of skill in the art may readily select other RNA blocking agents.

The samples are prepared by contacting blood (e.g., about 100 µL) with a suitable concentration of the blocking agent. For example, one suitable amount of blocking agent is between about 0.1 mM to about 10 mM, for example, 0.88 mM, of Ho-33342 reagent. The sample may be contacted with the selected blocking agent for between about 15 seconds to about 60 minutes. Incubation times may range from about 15 seconds to about 5 minutes, but 1 minute has been found to be adequate for this step of the method. As demonstrated in Example 2 below, 2 µL of a 25 mg/mL stock blocking agent per 100 µL blood with 20 minutes staining at 37° C. was sufficient. Further the incubation temperature ranges between 18° C. to 40° C., but may ordinarily be room temperature, i.e., about 23° C., for this step. One of skill in the art may anticipate that the temperature and incubation ranges may change somewhat depending upon the identity of the dye or enzyme used as the blocking agent. Such changes do not constitute new matter and would be understood by the skilled artisan.

By pre-exposure to the blocking agent, specific nucleic acid is prevented from binding to the red permeant dyes used in the subsequent method steps. Certain agents are fluorescent dyes which bind to the specific nucleic acid and do not emit in the red wavelength. Other agents are enzymes which digest the specific nucleic acid, also make it unavailable for binding by the red permeant dye used in this invention.

Following this blocking agent incubation, the method further involves contacting the pre-exposed sample with the cell-permeant, red excited SYTO dyes as described in the first method, without significantly disrupting the integrity of said cells. If the blocking agent is DNA specific, the SYTO dye will bind to the remaining RNA molecules. If the blocking agent is RNA specific, the SYTO dye will bind to remaining DNA molecules in the cell. After the cell populations in the sample are adequately stained with the red-excited dyes, the sample is excited with light in a single red wavelength and the fluorescence measured substantially as described in the first method above. Fluorescence emitted from one cell population in the sample is distinguishable from the fluorescence emitted from another cell population in the sample. Fluorescence is also measured in any of the conventional methods mentioned above. As described in more detail in Example 2 below, the result of this method in the analysis of WBC subpopulations according to the invention shifts the neutrophil populations relative to either the lymphocyte or monocyte populations, thereby enhancing the lymphocyte-neutrophil or neutrophil-monocyte separation and enhancing the analytic results, depending upon the specific dye combination used. It is anticipated that similar results are achievable using a variety of the red-excited dyes and in populations other than the WBC subpopulations illustrated in the example.

This embodiment of this method of the present invention displays the same advantages recited above for the first method. In addition, accuracy of specific measurements in increased by eliminating or reducing contributions from interfering substances in a sample.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

White Blood Cell Differentiation

This example demonstrates the use of SYTO® dyes for resolving white blood cell subpopulations based on nucleic acid staining and fluorescence measurement at one wavelength.

One hundred microliters of whole blood were stained with various concentrations (1, 2, 5, 10, and 20 µL) of SYTO®59 or SYTO®62 dyes [Molecular Probes, Inc.] for 1 minute on a mixer. Cells were excited at 632.8 nm (HeNe laser) and fluorescence (FL2), side scatter (SS) and forward scatter (FS) were measured for each sample in an XL flow cytometer [Coulter Corp.]. Fluorescence was measured at 675 nm for SYTO®62 stained cells and at 660 nm for SYTO®59 stained cells.

Figure 1B:
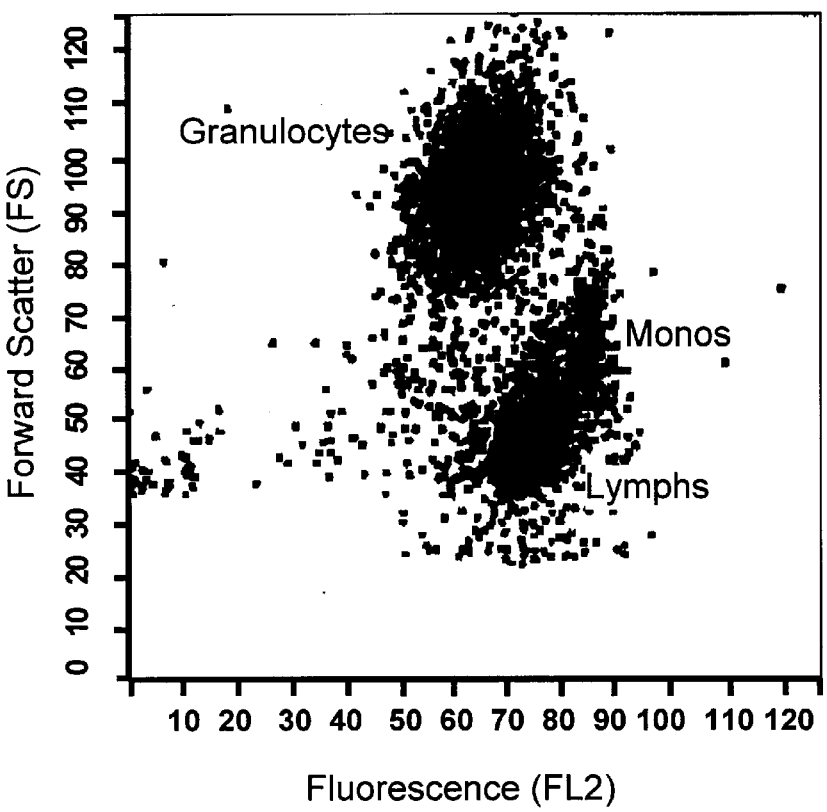
FIG. 1B is a two dimensional dot plot showing forward light scatter versus fluorescence signals for WBC stained with SYTO®59 stain and measured at one wavelength according to the present method.
Figure 2A:
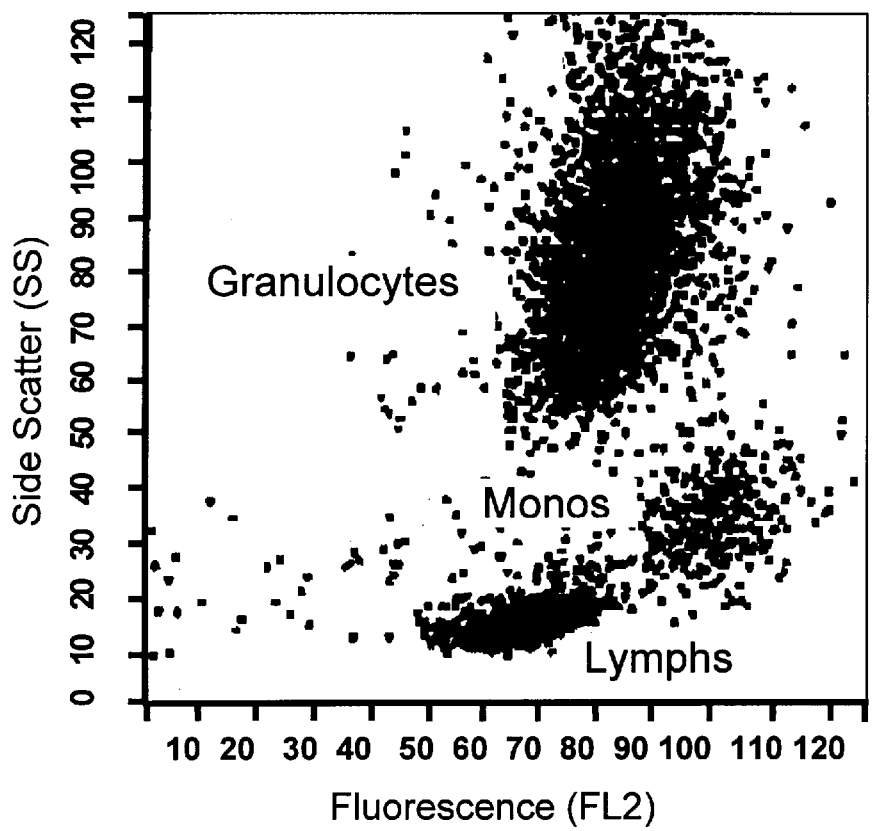
FIG. 2A is a two dimensional dot plot showing side light scatter vs. fluorescence signals for a sample of WBC stained with SYTO®62 stain and measured at one wavelength according to the present invention. Granulocytes, monocytes and lymphocytes are shown differentially stained.
Figure 2B:
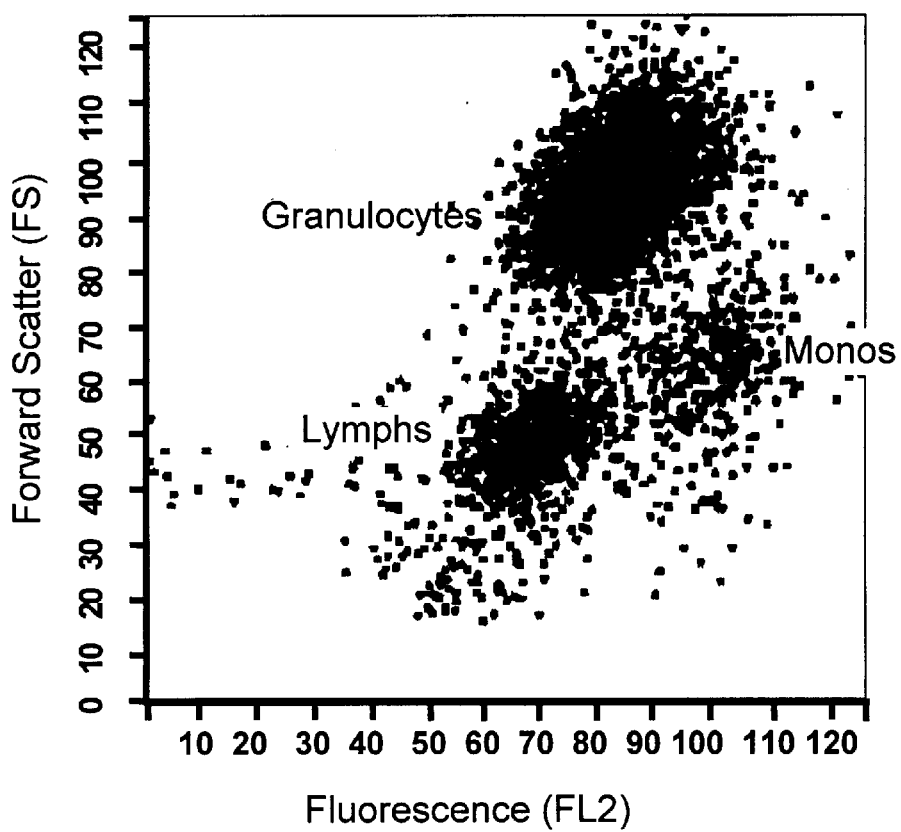
FIG. 2B is a two dimensional dot plot showing forward light scatter versus fluorescence signals for WBC stained with SYTO®62 stain and measured at one wavelength according to the present method.

The data illustrated in FIGS. 1A, 1B, 2A and 2B show the differential staining for SYTO®59 dye and SYTO®62 dye. The emission collected for fluorescence is 675 nm. FIGS. 1A and 2A show the 2D plots of Fluorescence vs. Side Scatter for SYTO®959 dye and SYTO®62 dye, respectively. FIGS. 1B and 2B show the 2D plots of Fluorescence vs. Forward Light Scatter for SYTO®59 dye and SYTO®62 dye, respectively.

From FIGS. 1A, 1B, 2A and 2B, it is clear that fluorescence from the nucleic acid dyes SYTO®59 dye or SYTO®62 dye, bound to cells, is different for the three WBC populations shown, i.e., granulocytes, monocytes and lymphocyte subpopulations. From the present experiment, it was discovered that 10 µL dye per 100 µL blood with 1 minute staining was sufficient to observe differential staining between these WBC populations. This is contradictory to the well known principle that a DNA specific dye should not be able to differentiate normal WBC subpopulations because each mature and normal WBC is supposed to have same amount of DNA.

The fact that both SYTO®62 dye and SYTO®59 dye show differences in fluorescence from these three populations is attributed to the ability of these SYTO® dyes to stain not only the DNA in the nucleus, but also the RNA and cytoplasm of the cell. Since the latter component is different for each population, the total number of dyes molecules bound to each population may not be the same even if the DNA content is the same. As a result, the total fluorescence intensity varies from population to population.

Furthermore, since the present experiments are conducted in a timed staining protocol, kinetics can also play a role in differential uptake of the dye in different subpopulation. Finally, based on these experiments and the nonspecificity for DNA alone, the inventors have determined that the SYTO® dyes can be very effective in differentiating abnormal or immature cell types that contain varying amounts of RNA.

EXAMPLE 2

Shifting of Cell Populations Using SYTO® Dyes in Combination With a DNA Blocking Agent As described above in Example 1, fluorescence from the nucleic acid SYTO®59 dye or SYTO®62 dye bound to cells comes not only from dye molecules bound to nuclear DNA but also from other components of the cell, such as cytoplasm or RNA in the cell. The present example demonstrates another aspect of this invention, i.e., that one can shift cell populations around if different specific components are blocked for staining prior to treating the cells to the SYTO® dyes. In this instance a DNA specific dye Ho-33342 [Sigma B-2261], which is known to have specific affinity for AT base pairs of DNA was employed as a blocking agent for cellular DNA. This dye absorbs in the ultra violet (UV) wavelength and emits in the blue wavelength. Therefore, when excited in the red wavelength, no fluorescence results from this dye and it simply serves as a blocking agent for the DNA.

One hundred microliters of whole blood was stained with 2 μL Ho-33342 DNA blocking agent or 2 μL IsoFlow™ as a control. The samples were then incubated for 20 minutes at 37° C. After staining with the DNA blocker, cells were stained for 1 minute with mixing for one of the following the dyes, SYTO®59 dye, SYTO®61 dye and SYTO®62 dye. Cells were then subjected to an automated rapid lyse process of about 30 seconds to one minute in duration for red cells mediated by formic acid [Coulter Corp.] for preparing WBCs for analysis in XL flow cytometer, and analyzed.

Figure 3A:
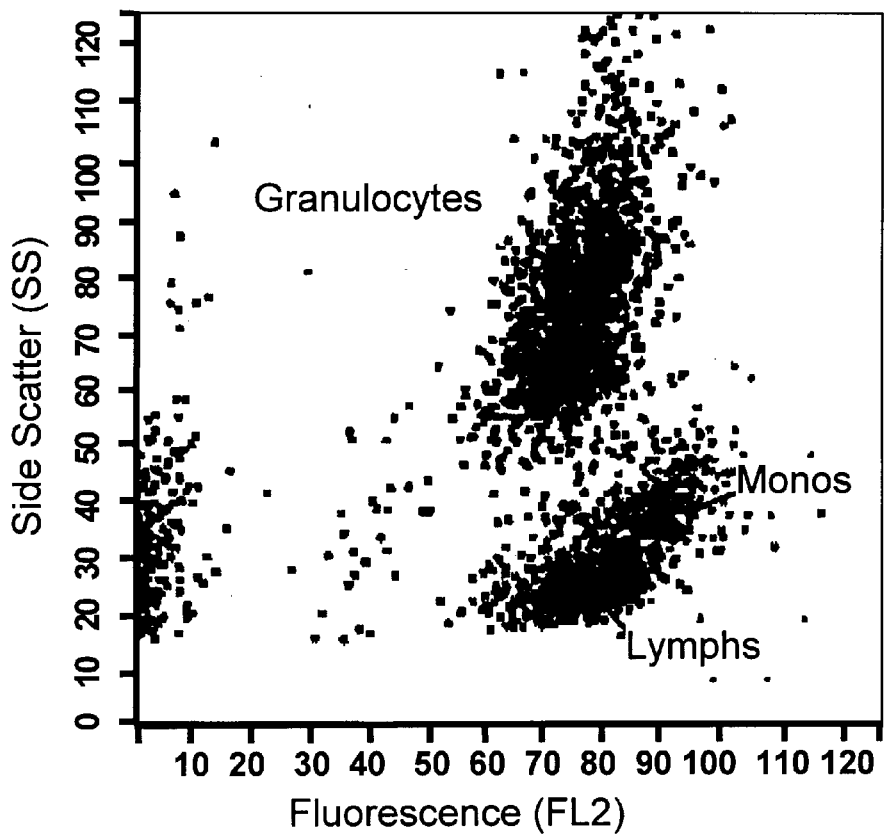
FIG. 3A is a two dimensional dot plot showing forward light scatter vs. fluorescence signals for a sample of WBC, which was not treated with a cellular DNA blocking agent, Ho-33342 [Sigma], prior to being stained with SYTO®59 stain and measured at one wavelength according to the present invention. Granulocytes, monocytes and lymphocytes are shown differentially stained.
Figure 3B:
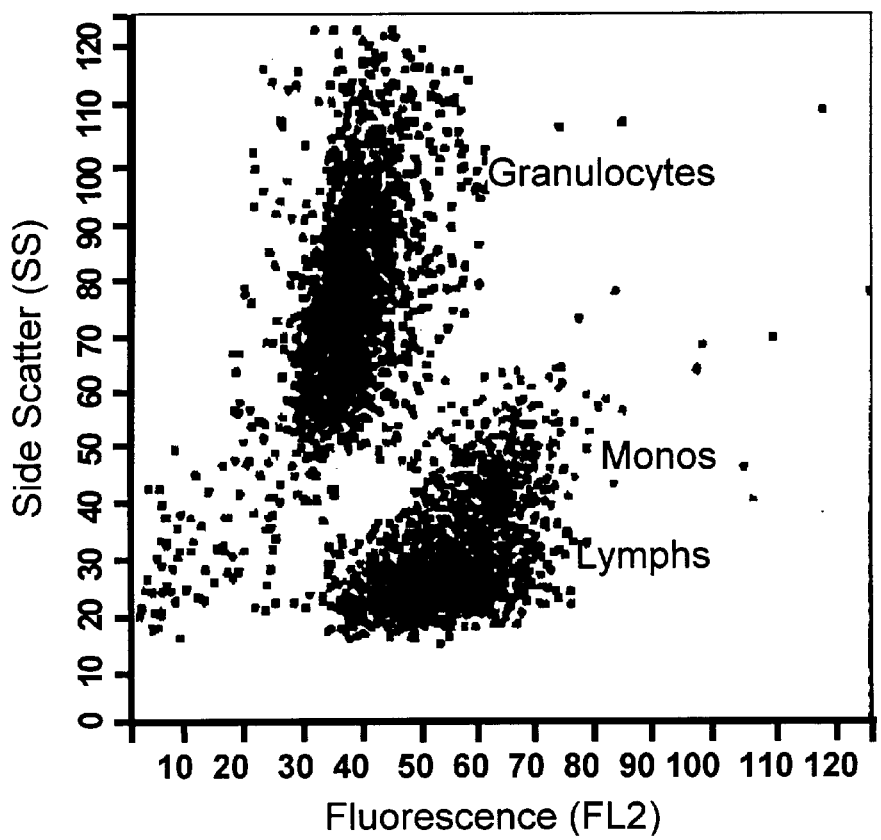
FIG. 3B is a two dimensional dot plot showing forward light scatter versus fluorescence signals for WBC treated with the cellular DNA blocking agent, Ho-33342 [Sigma], prior to being stained with SYTO®59 stain and measured at one wavelength according to the present method. The granulocyte cluster is shifted to the left relative to the lymphocyte cluster.
Figure 4A:
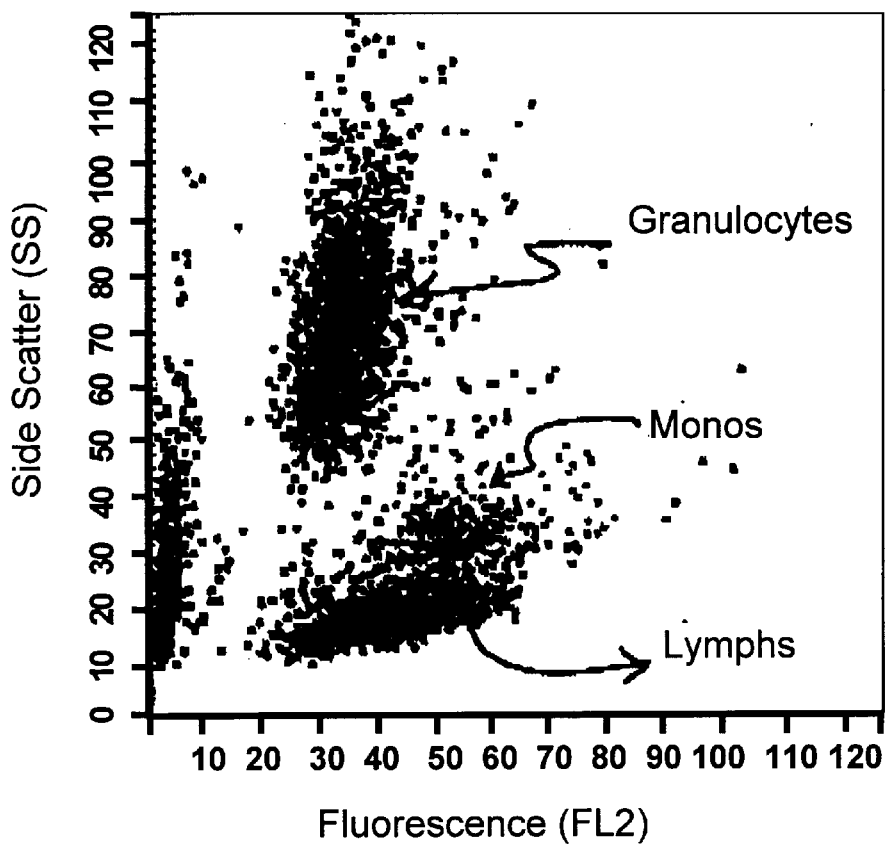
FIG. 4A is a two dimensional dot plot showing forward light scatter vs. fluorescence signals for a sample of WBC, which was not treated with the cellular DNA blocking agent, Ho-33342 [Sigma], prior to being stained with SYTO®61 stain and measured at one wavelength according to the present invention. Granulocytes, monocytes and lymphocytes are shown differentially stained.
Figure 4B:
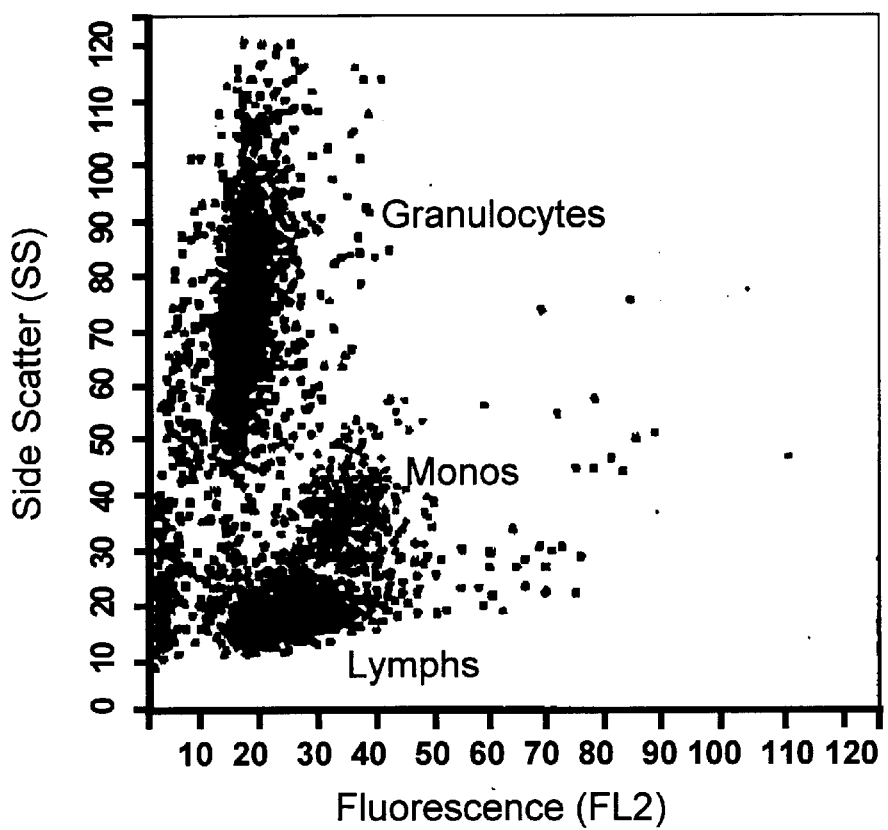
FIG. 4B is a two dimensional dot plot showing forward light scatter versus fluorescence signals for WBC treated with a cellular DNA blocking agent, Ho-33342 [Sigma], prior to being stained with SYTO®61 stain and measured at one wavelength according to the present method. No relative shift between lymphocytes and granulocytes is observed.
Figure 5A:
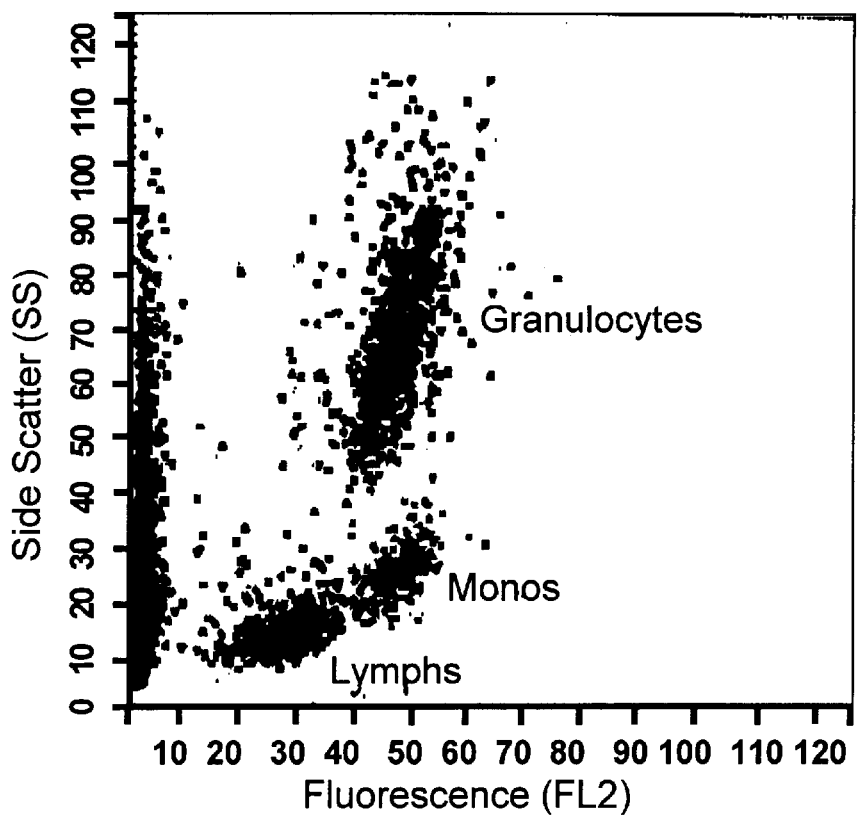
FIG. 5A is a two dimensional dot plot showing forward light scatter vs. fluorescence signals for a sample of WBC, which was not treated with a cellular DNA blocking agent, Ho-33342 [Sigma], prior to being stained with SYTO®62 stain and measured at one wavelength according to the present invention. Granulocytes, monocytes and lymphocytes are shown differentially stained.
Figure 5B:
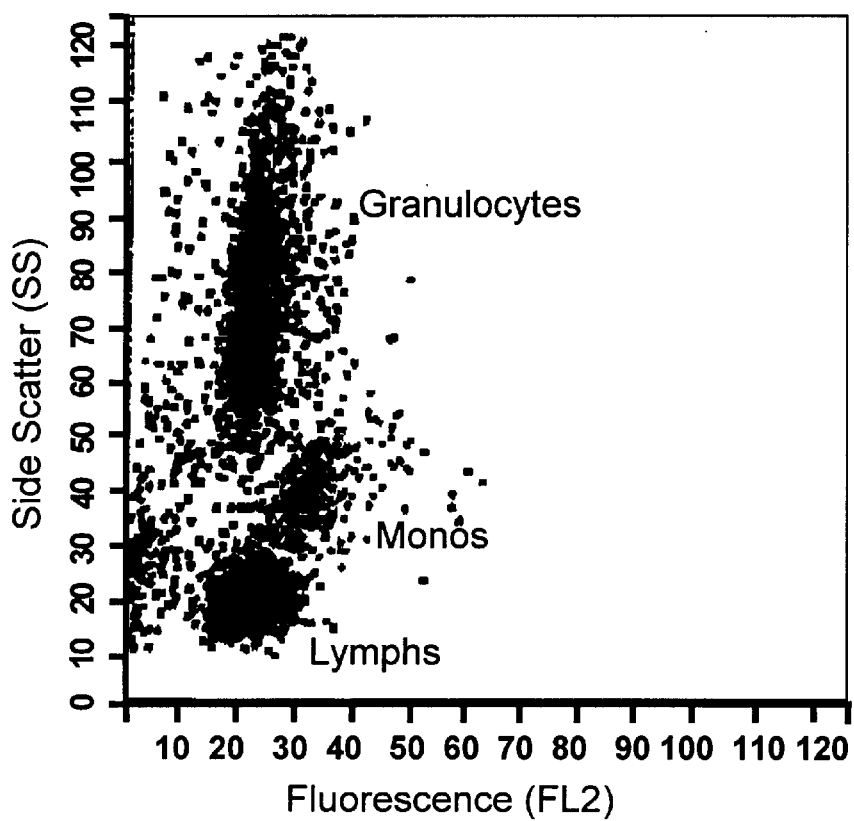
FIG. 5B is a two dimensional dot plot showing forward light scatter versus fluorescence signals for WBC treated with a cellular DNA blocking agent, Ho-33342 [Sigma], prior to being stained with SYTO®62 stain and measured at one wavelength according to the present method. Relative separation between granulocytes and monocytes is increased at the expense of lymphocyte-granulocyte separation.

The data shows the differential staining for these SYTO® dyes with (FIGS. 3B, 4B and 5B) and without (FIGS. 3A, 4A and 5A) pretreatment with the DNA blocking dye. The emission collected for fluorescence is 675 nm. In each case there is reduced staining suggesting some, but not all, staining is attributed to DNA. In addition, for SYTO®59 dye, the neutrophil populations shifts relative to the lymphocyte population, thereby enhancing the lymphocyte-neutrophil separation. The shift of the neutrophil population is even more significant in the case of SYTO®62 dye. In this case, such shift increases neutrophil-monocyte separation at the expense of separation between the lymphocytes and the neutrophils. For SYTO®61 dye, pre-treatment with Ho-33342 reagent reduces the overall SYTO®61 fluorescence from all populations, but the relative separation between subpopulations remained approximately the same.

These experiments show that the differential shifting and the resulting changes in resolution of cell population depend on specific SYTO® dyes used, taking into account the differences between these dyes in terms of the affinity for nuclear DNA and other components of the cell.

EXAMPLE 3

Reticulocyte Differentiation

Cells were stained by adding 2 μL of a 5 mM stock solution of SYTO®62 dye to 2 μL whole blood in 1 ml IsoFlow reagent (i.e., a non-fluorescent balanced electrolyte solution described in U.S. Pat. No. 3,962,125) and incubating the mixture for approximately 1 minute. Thereafter the cells were analyzed in an XL flow cytometer equipped with a red HeNe laser, with approximately 11.5 mW power incident on the beam shaping optics. Forward light scatter (FS), side scatter (SS) and one fluorescence (FL) parameter in the orthogonal direction were measured to analyze the red cells. The filter setup included a 600 DCLP, 633 LB, 675 BP, and mirror at 45° to collect SYTO®62 dye emission into a PMT.

Figure 6A:
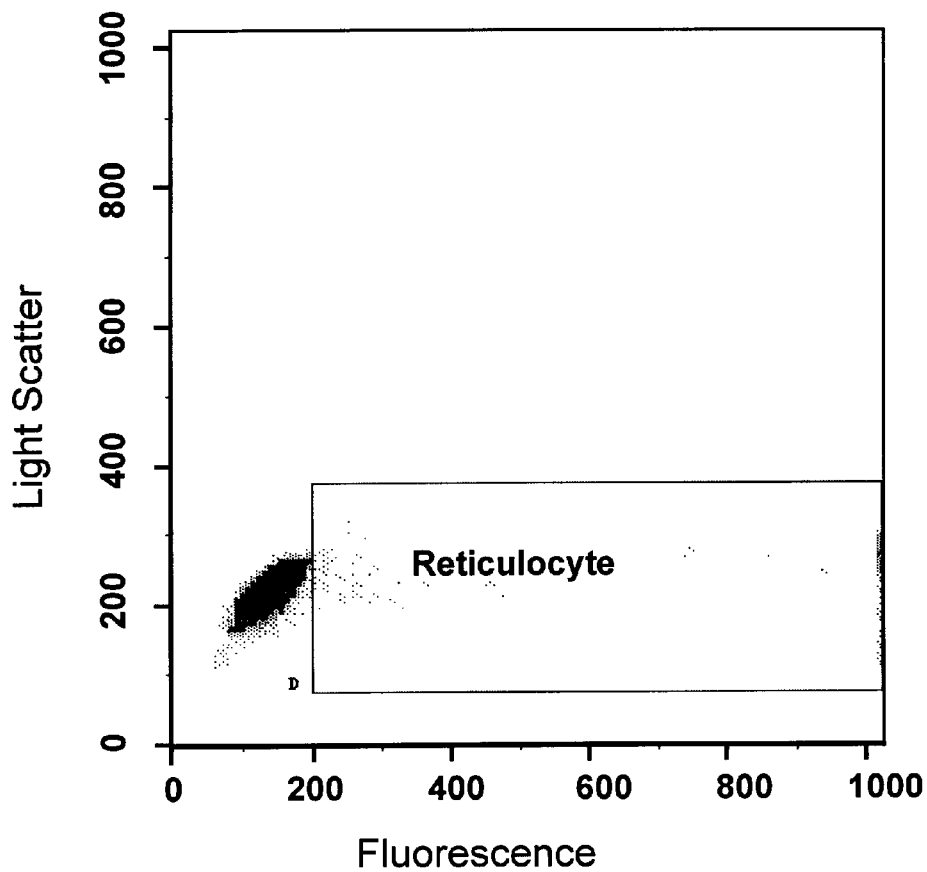
FIGS. 6A through 6E show the principle behind the analysis procedure to enumerate reticulocytes.
Figure 6B:
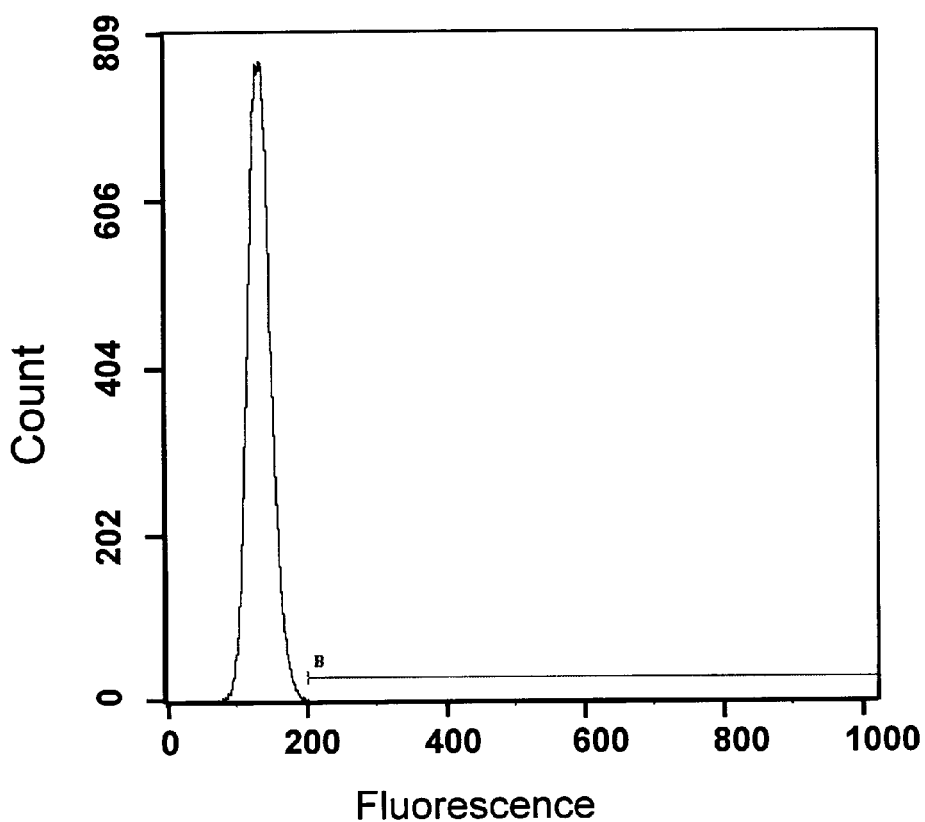

Bright red fluorescence in the 675 nm band resulted from a population of red cells. This indicated the presence of nucleic acid bound SYTO®62 stain in such cells. This fluorescence was attributed to SYTO®62 stained reticulocytes. The red cells were gated on SS vs FS dotplot. A fixed gate was then used to enumerate reticulocytes on a FL vs. FS dotplot, as shown in FIG. 6E, for example. Thus, reticulocytes stained with SYTO®62 stain using the present method are resolved from the mature red cells by the high fluorescence signal from the RNA bound SYTO®62 stain.

Figure 6C:
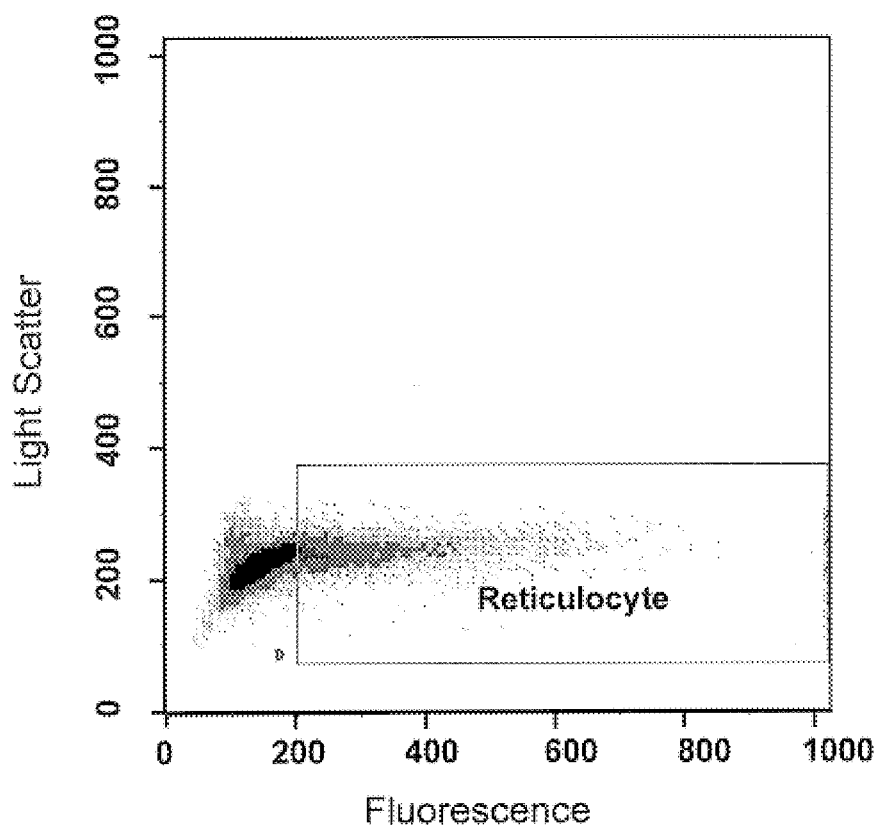
Figure 6D:
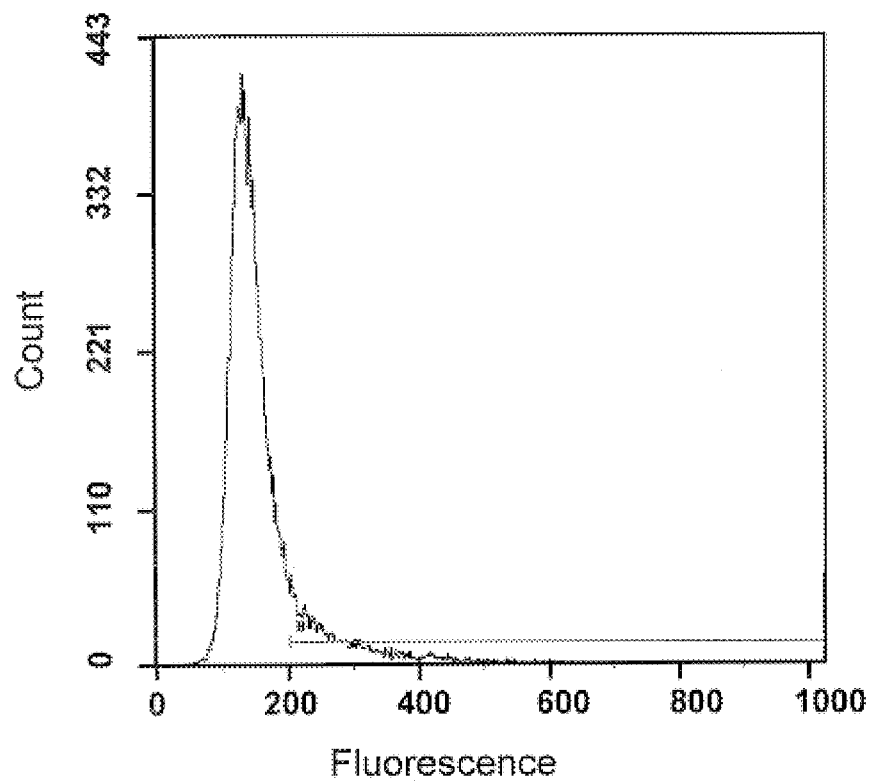
Figure 6E:
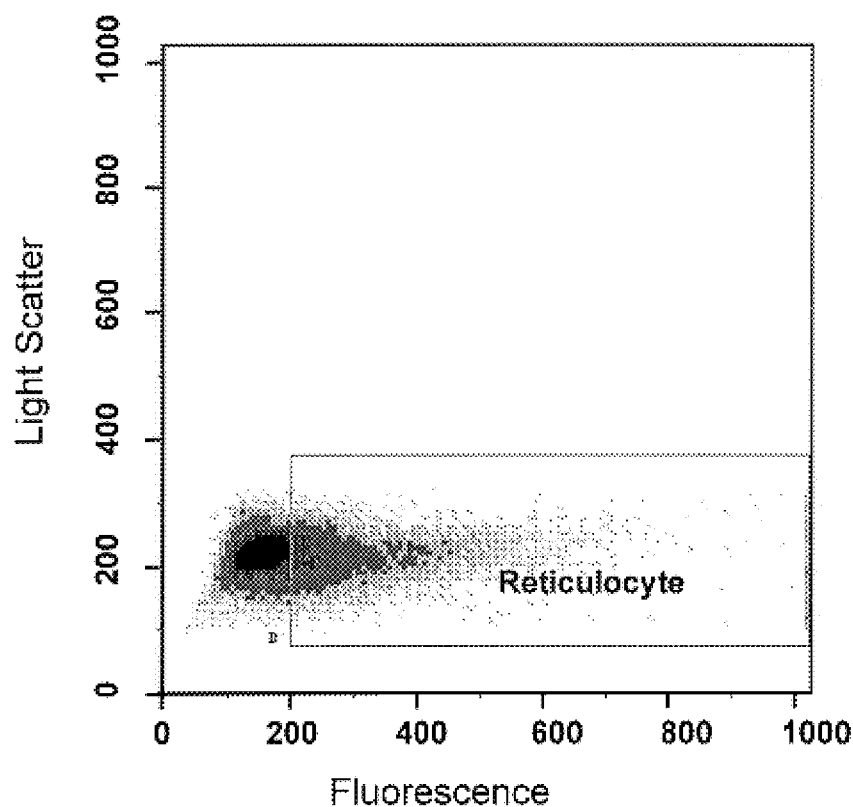
Figure 6F:
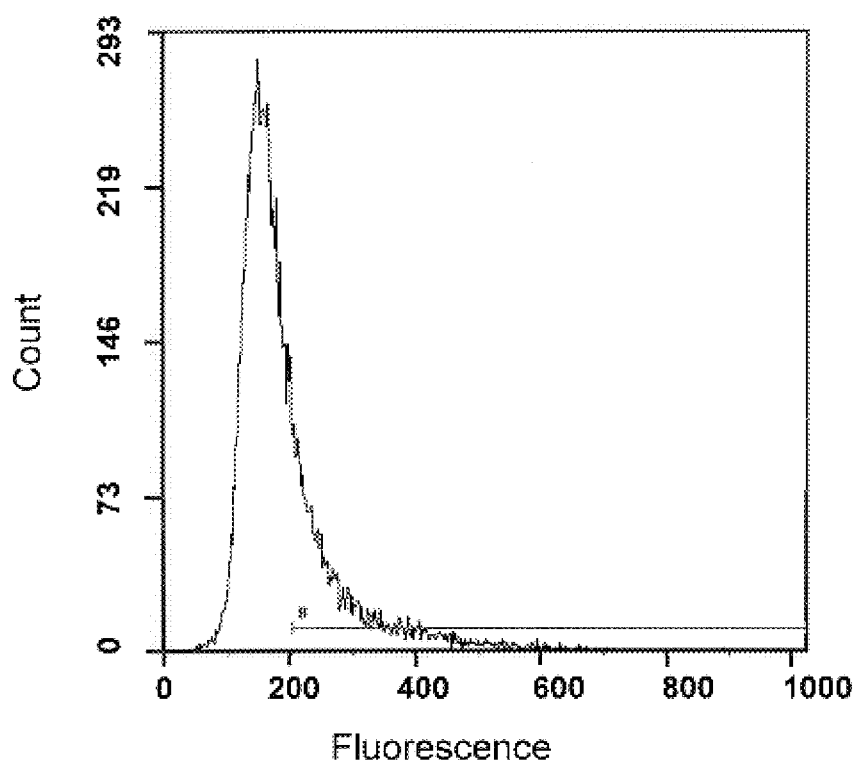
FIG. 6F is a one dimensional histogram of the sample described in FIG. 6E; the signal from the reticulocytes appear as a distinct tail on the right hand side.

The distribution of the cells in a forward scatter vs. fluorescence dotplot, shown for example in FIG. 6C, was consistent with the distribution of mature red cells and reticulocytes previously shown by Tanke et al., cited above, in relation to their work on Pyronin Y based reticulocyte measurements. In one dimensional histograms, this fluorescence appears as distinct tail on the right hand side of each fluorescence histogram prepared for samples containing low (FIG. 6B), medium (FIG. 6D), and high (FIG. 6F) reticulocyte counts.

1. Prior Art Methods

The above results obtained by the method of the present invention were compared to those obtained by the staining method employing a blue-excited illumination and the dye CPO according to the description of U.S. Pat. No. 5,639,666. Measurements for the CPO method were conducted in a standard XL flow cytometer using a 488 nm argon laser as the excitation (illumination) source. Forward scatter, side scatter and two fluorescence parameters were measured to analyze the red cells stained with CPO. Fluorescence was increased in two different color bands, 525 nm (for DNA bound CPO) and 675 nm (for RNA bound CPO). The red cells were gated on SS vs. FS dotplot. An automated gating algorithm, available in commercial XL flow cytometers, calculated reticulocyte percentage from a DNA vs. RNA fluorescence dotplot.

Figure 7:
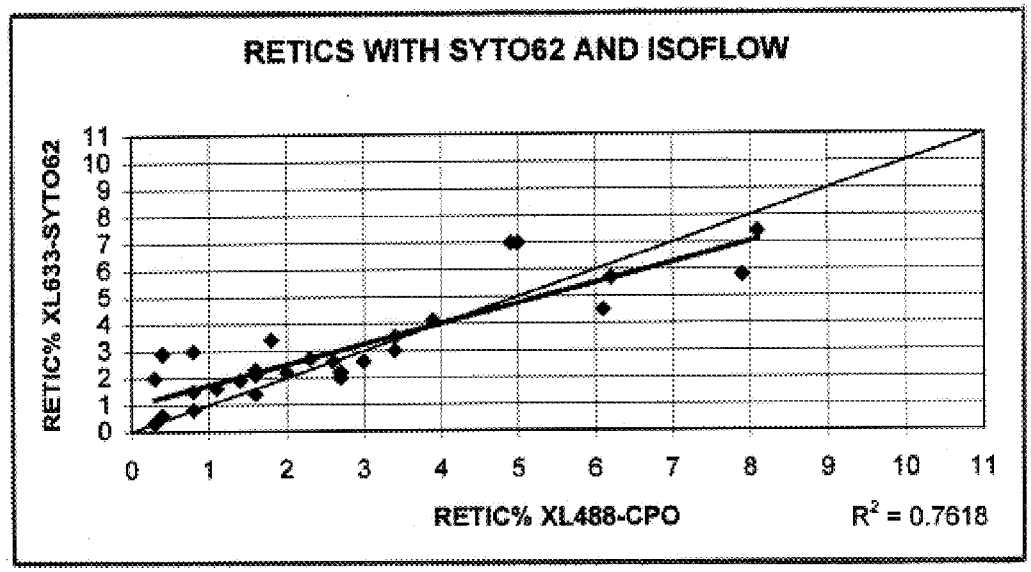
FIG. 7 is a graph correlating two sets of results: the results obtained by the present SYTO®62 stain based method and the results obtained using the CPO staining method described in U.S. Pat. No. 5,639,666. Measurements for CPO method were conducted in a standard XL™ flow cytometer using a 488 nm argon laser as the excitation source. See Example 3 below.

Comparison of the results obtained according to the present method and the results obtained by independent measurements based on CPO fluorescence in a standard XL flow cytometer are correlated in FIG. 7, in which the percentage of the fluorescent subpopulation corresponded closely to reticulocyte percentage for each sample enumerated. This well behaved trend is observed in the correlation between the two sets of results.

2. Use of Other SYTO® Dyes in the Present Method

Figure 8:
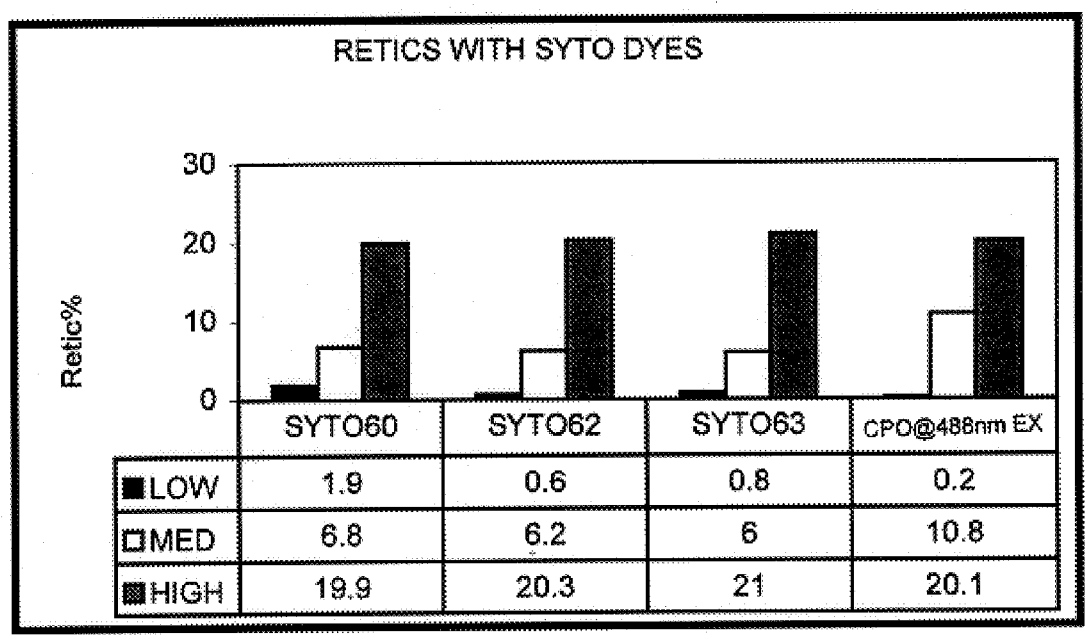
FIG. 8 is a bar graph demonstrating that other red-excited dyes, i.e., SYTO®60, SYTO®63, as well as SYTO®62, can be used to stain reticulocytes as described above in FIGS. 6A–7. For comparison, the dye CPO excited at 488 nm is also reproduced on this graph.

Finally, other red-excited, cell permeant dyes, namely SYTO®60 stain and SYTO®63 stain can be used as reticulocyte stains according to the method of this invention. The results obtained for these dyes for whole blood samples with high, medium and low reticulocyte percentages are reported in FIG. 8.

All publications cited in this specification are indicative of the level of skill of those in the art to which this application pertains and are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for enumerating and distinguishing blood cell populations in a biological sample comprising the steps of:
   (A) contacting a biological sample containing two or more blood cell populations with a selective nucleic acid-specific blocking agent to form a sample mixture;
   (B) contacting the sample mixture of step (A) with a cell membrane-permeant, red-excited dye without significantly disrupting cellular integrity of said cells to form a dyed sample mixture;

(C) exciting said dyed sample mixture with light in a single red wavelength; and (D) measuring fluorescence emitted from different cell populations in said dyed sample mixture, wherein the fluorescence emitted from one blood cell population is distinguishable from the fluorescence emitted from another blood cell population in said sample.

2. The method according to claim 1 wherein said cell populations comprise white blood cells (WBC).

3. The method according to claim 2 wherein said WBC are selected from the group consisting of immature granulocytes, lymphocytes, neutrophils, eosinophils, basophils, monocytes, abnormal lymphocytes, blast cells, band cells, myelocytes, promyelocytes and metamyelocytes.

4. The method according to claim 1 wherein said blood cell populations are red blood cells (RBC).

5. The method according to claim 4 wherein said RBC are selected from the group consisting of mature red cells, reticulocytes and NRBC.

6. The method according to claim 1, wherein said light is emitted from a source selected from the group consisting of a diode laser, a light emitting diode (LED), an ion laser, an upconversion fiber laser, an upconversion solid state laser, a dye laser, and a lamp.

7. The method according to claim 1 wherein said biological sample is selected from the group consisting of whole blood, plasma, and serum.

8. The method according to claim 1 wherein said sample is excited and fluorescence is measured by a flow cytometer.

9. The method according to claim 1 wherein said fluorescence in said sample is measured by a fluorescence microscope.

10. The method according to claim 1 wherein steps (A)–(D) are automated.

11. The method according to claim 1 which is performed by an apparatus which measures fluorescence on a cell-by-cell basis.

12. The method according to claim 1, which is performed by an apparatus which comprises detection means selected from the group consisting of PMTs, semiconductor based PIN detector, and semiconductor based APD detector.

13. The method according to claim 1 wherein said nucleic acid specific blocking agent is specific for DNA.

14. The method according to claim 13 wherein said agent is selected from the group consisting of DNA dyes which fluoresce in wavelengths other than the red wavelength of step (C) and enzymes that selectively digest DNA.

15. The method according to claim 1 wherein said nucleic acid specific blocking agent is specific for RNA.

16. The method according to claim 15 wherein said agent is selected from the group consisting of RNA dyes which fluoresce in wavelengths other than the red wavelength of step (C) and enzymes that selectively digest RNA.

17. The method of claim 1 which further comprises lysing red blood cells after contacting the sample mixture of step (A) with a cell membrane-permeant, red-excited dye.

18. The method according to claim 1, which is performed by an apparatus which measures fluorescence simultaneously with other parameters selected from the group consisting of light scatter, DC and RF.

* * * * *